US00PP16874P2

(12) United States Plant Patent
Kievit

(10) Patent No.: US PP16,874 P2
(45) Date of Patent: Jul. 25, 2006

(54) ***CALIBRACHOA* PLANT NAMED 'KIECASFLIROB'**

(50) Latin Name: *Calibrachoa procumbens*
Varietal Denomination: Kiecasflirob

(75) Inventor: Christa Kievit, Venhuizen (NL)

(73) Assignee: Kieft Bloemzaden B.V., Venhuizen (NL)

( * ) Notice: Subject to any disclaimer, the term of this patent is extended or adjusted under 35 U.S.C. 154(b) by 0 days.

(21) Appl. No.: 11/108,580

(22) Filed: Apr. 15, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Calibrachoa* plant named 'Kiecasflirob', characterized by its uniform, low spreading, mounded and trailing plant habit; freely and continuous branching habit; dense and bushy plant growth habit; freely and continuous flowering habit, numerous small dark violet-colored flowers with dark purple-colored centers and golden yellow-colored throats; and good garden performance.

1 Drawing Sheet

Botanical designation: *Calibrachoa procumbens.*
Cultivar denomination: 'Kiecasflirob'.

BACKGROUND OF THE INVENTION

The present Invention relates to a new and distinct cultivar of *Calibrachoa* plant, botanically known as *Calibrachoa procumbens*, and hereinafter referred to by the cultivar name Kiecasflirob.

The new *Calibrachoa* is a product of a planned breeding program conducted by the Inventor in Venhuizen, The Netherlands. The objective of the breeding program is to create new trailing *Calibrachoas* with numerous flowers with attractive non-fading flower colors and tolerance to high temperatures.

The new *Calibrachoa* originated from a cross-pollination made by the Inventor during in 2002 of a proprietary *Calibrachoa* seedling selection identified as 530-2, not patented, as the female, or seed, parent with the *Calibrachoa* cultivar Carillion Carmine, unpatented, as the male, or pollen, parent. The new *Calibrachoa* was selected as a single flowering plant from the resulting progeny of the stated cross-pollination by the Inventor in a controlled environment in 2002 in Venhuizen, The Netherlands.

Asexual reproduction of the new cultivar by terminal cuttings taken in Venhuizen, The Netherlands since 2003 has shown that the unique features of this new *Calibrachoa* are stable and reproduced true to type in successive generations.

SUMMARY OF THE INVENTION

Plants of the cultivar Kiecasflirob have not been observed under all possible environmental conditions. The phenotype may vary somewhat with variations in environment such as temperature and light intensity without, however, any variance in genotype.

The following traits have been repeatedly observed and are determined to be the unique characteristics of 'Kiecasflirob'. These characteristics in combination distinguish 'Kiecasflirob' as a new and distinct cultivar:

1. Uniform, low spreading, mounded and trailing plant habit.
2. Freely and continuous branching habit; dense and bushy plant growth habit.
3. Freely and continuous flowering habit, numerous small dark violet-colored flowers with dark purple-colored centers and golden yellow-colored throats.
4. Good garden performance.

Plants of the new *Calibrachoa* and the parents differed in flower coloration.

Plants of the new *Calibrachoa* can be compared to plants of the *Calibrachoa* cultivar Carillion Carmine, not patented. In side-by-side comparisons conducted in Venhuizen, The Netherlands, plants of the new *Calibrachoa* differed from plants of the cultivar Carillion Carmine in the following characteristics:

1. Plants of the new *Calibrachoa* had darker violet-colored flowers than plants of the cultivar Carillion Carmine.
2. Plants of the new *Calibrachoa* were more high temperature tolerant than plants of the cultivar Carillion Carmine.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Calibrachoa.*

The photograph at the bottom of the sheet comprises a side perspective view of a typical flowering plant of 'Kiecasflirob' grown in a container.

The photograph at the top of the sheet comprises a close-up view of typical flowers and leaves of 'Kiecasflirob'.

DETAILED BOTANICAL DESCRIPTION

The aforementioned photographs and following observations and measurements describe plants grown in Lompoc, Calif., under commercial practice during the winter and spring in a polycarbonate-covered greenhouse with day temperatures ranging from 21 to 24° C., night temperatures ranging from 16 to 18° C., and light levels ranging from 4,000 to 8,000 foot candles. When the photographs and the description were taken, plants had been growing for about 13 weeks with one plant per 10-cm container.

Botanical classification: *Calibrachoa procumbens* cultivar Kiecasflirob.

Parentage:

*Female parent.*—Proprietary *Calibrachoa procumbens* seedling selection identified as 530-2, not patented.

*Male parent.*—*Calibrachoa procumbens* cultivar Carillion Carmine, not patented.

Propagation:

*Type cutting.*—Terminal vegetative cuttings.

*Time to initiate roots, summer and winter.*—About two weeks at 21° C.

*Time to develop roots.*—About three weeks at 21° C.

*Root description.*—Fine, fibrous; white in color.

*Rooting habit.*—Freely branching; dense.

Plant description:

*Form.*—Annual flowering plant; uniform, mounded, low spreading and trailing plant habit; plants eventually becoming hemispherical to spherical in shape. Freely and continuously branching habit with about six main lateral branches per plant each with about four to five secondary branches; dense and bushy plant growth habit. Vigorous growth habit.

*Plant height.*—About 7 cm.

*Plant diameter.*—About 36 cm.

*Lateral branches.*—Length: About 28 cm. Diameter: About 2.5 mm. Internode length: About 2.2 cm. Texture: Pubescent. Color: 144B.

*Foliage description.*—Arrangement: Before flowering, alternate; after flowering, opposite; simple. Length: About 3.2 cm. Width: About 8 mm. Shape: Narrowly elliptic. Apex: Rounded. Base: Attenuate. Margin: Entire. Texture, upper and lower surfaces: Pubescent; slightly glandular. Venation pattern: Pinnate, arcuate. Color: Developing foliage, upper surface: 146A. Developing foliage, lower surface: 146B. Fully expanded foliage, upper and lower surfaces: 146A. Venation, upper and lower surfaces: 146B. Petiole length: About 6 mm. Petiole diameter: About 1 mm. Petiole color: 146B.

Flower description:

*Flower type and habit.*—Salverform flowers; single, axillary. Flowers face mostly upward or outward and are held above and beyond the foliage.

*Quantity of flowers.*—Freely flowering, typically about five open flowers and flower buds per lateral stem.

*Natural flowering season.*—Long day responsive; spring until frost in the autumn; flowering continuous during the flowering period. Flowers persistent.

*Flower longevity on the plant.*—About four to five days. Fragrance: None detected.

*Flower diameter.*—About 3.1 cm.

*Flower throat diameter.*—About 8 mm.

*Flower tube length.*—About 2 cm.

*Flower tube diameter at base.*—About 2 mm.

*Flower buds* (*showing color*).—Length: About 2.1 cm. Diameter: About 4 mm. Shape: Elongated oblong. Color: More gray than 79A.

*Corolla.*—Arrangement/appearance: Single whorl of five petals, fused into flared trumpet with distinct clefts between petal lobes. Petal length from throat: About 1.2 cm. Petal width: About 1.4 cm. Petal shape: Roughly spatulate or fan-shaped. Petal apex: Rounded. Petal margin: Entire. Petal texture, upper and lower surfaces: Smooth, velvety. Color: Petal, upper surface, when opening: Brighter violet than 79A. Petal, lower surface, when opening: More gray than 79C. Petal, upper surface, fully opened: Brighter than 83A; towards the base, 79A. Petal, lower surface, fully opened: 79D. Flower throat (inside): 17C. Flower tube (outside): 160B. Venation, upper petal surface: 79A. Venation, lower petal surface: 79C. Venation, throat: 79A. Venation, tube: 79B.

*Sepals.*—Arrangement/appearance: Single whorl of five sepals fused at base, star-shaped. Length: About 1 cm. Width: About 2 mm. Shape: Narrowly lanceolate. Apex: Acute. Margin: Entire. Texture, upper and lower surfaces: Finely pubescent. Color, immature and mature, upper surface: 146B. Color, immature and mature, lower surface: 146C.

*Peduncles.*—Length: About 2 cm. Width: About 1 mm. Angle: About 30° to the stem. Strength: Strong. Texture: Pubescent. Color: 145A.

*Reproductive organs.*—Stamens: Quantity/arrangement: Five. Anther shape: Oval. Anther length: Less than 1 mm. Anther color: 10C. Pollen amount: Scarce. Pollen color: 10C. Pistils: Quantity: One. Pistil length: About 9 mm. Stigma shape: Rounded. Stigma color: 145B. Style length: About 6 mm. Style color: 145D. Ovary color: 145A.

*Seed/fruit.*—Seed and fruit production has not been observed.

Disease/pest resistance: Plants of the new *Calibrachoa* have not been noted to be resistant to pathogens or pests common to *Calibrachoa*.

Garden performance: Plants of the new *Calibrachoa* have good garden performance and have been observed to be tolerant to rain, wind and temperatures ranging from 5 to 35° C.

It is claimed:

1. A new and distinct cultivar of *Calibrachoa* plant named 'Kiecasflirob', as illustrated and described.

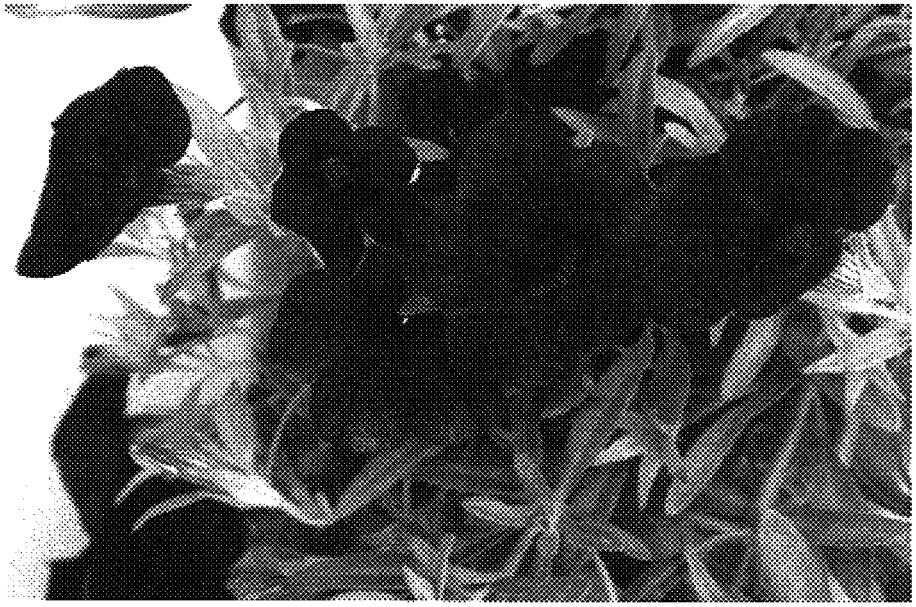
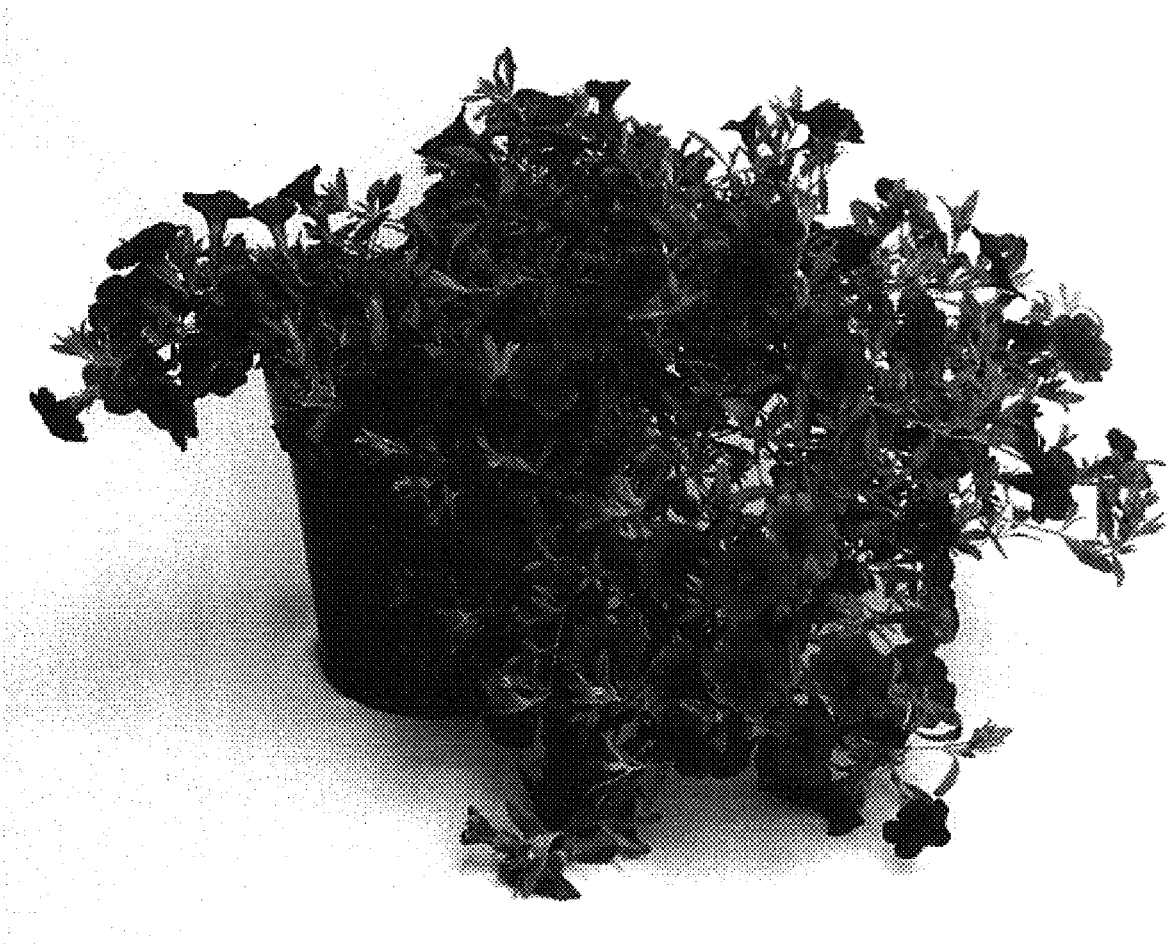

* * * * *